US007153866B1

(12) United States Patent
Mitchell et al.

(10) Patent No.: US 7,153,866 B1
(45) Date of Patent: Dec. 26, 2006

(54) USE OF TEMPOL FOR THE TREATMENT OF LI-FRAUMENI SYNDROME AND ATAXIA TELANGIECTASIA

(75) Inventors: James B. Mitchell, Damascus, MD (US); Angelo Russo, Bethesda, MD (US); Murali Krishna Cherukuri, Rockville, MD (US); Anne Marie DeLuca, Tucson, AZ (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/424,519

(22) PCT Filed: May 27, 1998

(86) PCT No.: PCT/US98/10685

§ 371 (c)(1),
(2), (4) Date: Mar. 3, 2000

(87) PCT Pub. No.: WO98/53835

PCT Pub. Date: Dec. 3, 1998

Related U.S. Application Data

(60) Provisional application No. 60/047,724, filed on May 27, 1997.

(51) Int. Cl.
*A61K 31/445* (2006.01)
*A61K 31/44* (2006.01)
*A61K 31/42* (2006.01)

(52) U.S. Cl. ............. 514/315; 514/330; 514/345; 514/376

(58) Field of Classification Search ........ 514/315, 514/256, 261, 352, 370, 377, 398, 406, 426, 514/427, 330, 345, 376
See application file for complete search history.

(56) References Cited

U.S. PATENT DOCUMENTS 5,840,734 A * 11/1998 Bernstein ............. 514/315

FOREIGN PATENT DOCUMENTS

WO    WO 96/40127    12/1996

OTHER PUBLICATIONS

"Structure and function of the p53 tumor suppressor gene: clues for rational cancer therapeutic strategies", Harris, 1996, 88:1442-55.*
"Antitumor activity of a new low immunosuppressive derivative of podophyllotoxin (GP-11) and its mechanism", Wang et al., 1993, Anti-Cancer Drug Des., 8(3), 193-202.*
"NINDS Ataxia Telangiectasia Information Page", The National Institute of Neurological Disorders and Stroke, NIH, 2003.*
"Genetic Testing on Embryos Hits New Milestone", Matloff, E., Reuters News, 2001.*
Simone, Oncology: Introduction, Cecil Textbook of Medicine, 20th Edition, vol. 1, pp. 1004-1010. 1996.*
"Atm-Deficient Mice: A Paradigm of Ataxia Telangiectasia", Cell, vol. 86, 159-171, Jul. 12, 1996.*
"Cancer Chemoprevention by the Antioxidant tempol in Atm-deficient mice", Schubert et al., Human Molecular Genetics, abstract, 2004, 13(16), 1793-1802.*
JAX Mice Data Sheet, www.jaxmice.jax.org, 2006.*
Monti et al., "Cytotoxicity of Tempol, a Piperidine Nitroxyde Spin Label, Against Different Neoplastic and Non-Neoplastic Cell Lines," *PAACR Annual Meeting*, 36, 387 (1995).
Monti et al., "DNA Damage and Apoptosis in Human Leukemic Cells Treated with the Piperidine Nitroxyde Tempol," *PAACR Annual Meeting*, 38, 193 (1997).
Monti et al., "The Piperidine Nitroxyde Tempol-Induced Apoptosis and P21-WAF1-CIP1 Expression in P53-Deficient Cells," *PAACR Annual Meeting*, 39, 90 (1998).

* cited by examiner

*Primary Examiner*—Brian Kwon
(74) *Attorney, Agent, or Firm*—Leydig, Voit & Mayer, Ltd.

(57) ABSTRACT

The present invention provides a method for the prophylactic and therapeutic treatment of cancer. The method comprises administering to an animal, preferably a mammal, more preferably a human, at risk for developing a cancer or having a cancer a nitroxide or a prodrug thereof, wherein the nitroxide or prodrug thereof preferably is alicyclic or heterocyclic and more preferably is a compound of Formula (I) or Formula (II): in an amount sufficient to prevent or treat said cancer, wherein said cancer is susceptible to prevention or treatment by said nitroxide or prodrug thereof. Also provided is a composition for use in the method

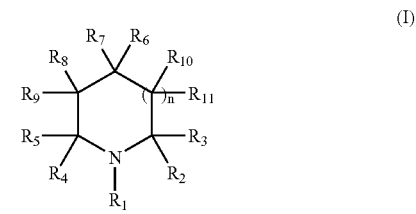
(I)

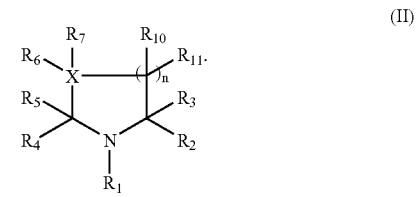

(II)

4 Claims, 2 Drawing Sheets

USE OF TEMPOL FOR THE TREATMENT OF LI-FRAUMENI SYNDROME AND ATAXIA TELANGIECTASIA

This application is a 371 of PCT/US98/10685, filed on May 27, 1998, which claims benefit of 60/047,724, filed May 27, 1997.

FIELD OF THE INVENTION

The present invention relates to nitroxides and prodrugs thereof and their use in the prophylactic and therapeutic treatment of cancer.

BACKGROUND OF THE INVENTION

Cancer is a major world-wide health problem. Given that the vast majority of human tumors are difficult to treat effectively, those afflicted suffer physically, emotionally and financially and inevitably die an early death. There is also a tremendous burden on the families and friends of those afflicted as well as on society at large. Accordingly, the ability to prevent cancer, delay its onset and/or slow its progression would benefit everyone.

Although extensive research around the world has led to advances in cancer treatment, progress has been slow and there is no known cure. However, modern molecular biological techniques have contributed to our understanding of the genetic aspects of cancer development. For example, the tumor suppressor gene p53, which is representative of a general class of genes that code for products that regulate cellular function by thwarting the cascade of events that causes a normally functioning cell to either die or become immortal, i.e., cancerous, has been shown to encode a transcription factor that suppresses tumor development. Mutations in the p53 tumor suppressor gene have been shown to affect the production of the oncogene-suppressing transcription factor. For example, either no transcription factor is produced or a transcription factor that is ineffectual or partially effective is produced. In fact, the p53 tumor suppressor gene is the most common site of genetic lesions in human cancers (Levine et al., Nature 351: 453–456 (1991); and Hollstein et al., Science 253: 49–53 (1991)), with more than half of all human tumors exhibiting p53 point mutations or deletions (Chang et al., Am. J. Gastroenterol. 88: 174–186 (1993)). Mutations in the p53 gene also have been associated with Li-Fraumeni syndrome, a familial autosomal dominant disease associated with an increased risk of tumorigenesis (Srivastava et al., Nature 348: 747–749 (1990)). The p53 protein also plays a role in the cellular response to DNA-damaging agents by facilitating in a block in the G1 phase of the cell cycle following DNA damage, thereby providing time for repair of the DNA damage (Pictenpol et al., Nature 365: 17–18 (1993); and Kuerbitz at al., PNAS USA 89: 7491–7495 (1992)) or by causing apoptosis (Yonish-Rouach et al., Nature 352: 345–347 (1991)).

In order to enable the further study of the p53 gene, recombinant DNA techniques have been used to develop rodent models. In one model, the rodents are homozygous for mutant p53 alleles (p53 −/−), such that the p53 gene is disrupted or "knock-out" (p53 −/−) and does not function, and the rodents are highly susceptible at an early age to a variety of tumors (Donehower et al., Nature 356; 251–221 (1992)). In another model, the rodents heterozygous for wild-type and mutant p53 alleles (p53 +/−) and, although they develop tumors 10–20 months after birth, they live considerably longer than the homozygous mutant p53 rodents (Harvey et al, Nature-Genetics 5: 225–229 (1993)). Exposure of these rodents to carcinogens, such as dimethylnitrosamine, or whole body irradiation accelerates tumor formation (Harvey et al. (1993), supra; and Lee et al., Oncogene 12: 3731–3736 (1994)).

Nitroxides are stable compounds, which are low in molecular weight, metal-independent, nontoxic and nonallergenic, and are characterized by low reactivity with oxygen, high solubility in aqueous solutions, and the ability to cross cellular membranes. The lipophilicity of nitroxides can be controlled by the addition of various organic substituents, in order to facilitate the targeting of the nitrides to specific organs or organelles.

Nitroxides have been shown to protect cells and animals against the untoward acute effects, such as cytotoxicity, of short-term exposure to lethal doses of free radicals and oxidative species, such as superoxide, hydrogen peroxide, hydroxyl radicals, and hydroperoxides, i.e., by functioning as antioxidants (U.S. Pat. No. 5,462,946). In cell culture, nitroxides have been shown to sensitize hypoxic cells to ionizing radiation and, paradoxically, protect aerobic cells from ionizing radiation. Also in cell culture, nitroxides have been shown to protect cells against the acute cytotoxic affects of paraquat and anti-neoplastic agents. Tempol, a nitroxide, has been shown to be cytotoxic against neoplastic cell lines in vitro (Monti et al., PAACR, 36: 387 (1995), and Monti et al., PAACR, 38: 193 (1997)). In animals, nitroxides have been shown to protect against radiation-induced alopecia and to induce weight loss. It has been reported that nitroxides can be used to protect against pulmonary adult respiratory distress syndrome, lenticular degeneration and hyaline membrane disease in infants, cataracts, oxidative stress, such as that associated with oxygen therapy or hyperbaric oxygen treatment, reperfusion injury, such as that associated with myocardial infarction, stroke, pancreatitis, intestinal ulceration, and organ transplantation.

It has now been surprisingly and unexpectedly discovered that nitroxides and prodrugs thereof are useful in the prophylactic and therapeutic treatment of cancer (i.e., prevention, delay of onset, and slowing of progression of cancer). Accordingly, it is an object of the present invention to provide a method for the prophylactic and therapeutic treatment of cancer. It is another object of the present invention to provide a composition for use in the method. These and other objects and advantages of the present invention, as well as additional inventive features, will be apparent from the description of the invention provided herein.

BRIEF SUMMARY OF THE INVENTION

The present invention provides a method for the prophylactic and therapeutic treatment of cancer. The method comprises administering to an animal, preferably a mammal, more preferably a human, at risk for developing a cancer or having a cancer, a nitroxide or a prodrug thereof in an amount sufficient to prevent or treat the cancer, respectively, wherein said cancer is susceptible to prevention or treatment with said nitroxide or said prodrug thereof. Preferably, the nitroxide or prodrug thereof is alicyclic or heterocyclic. More preferably, the nitroxide or prodrug thereof is a compound of Formula I or Formula II:

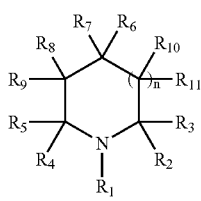

Formula I or

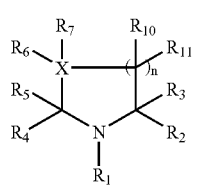

Formula II wherein $R_1$ is selected from the group consisting of H, OH, OZ, O., =O and Y, wherein Y is a leaving group, which can be converted to H, OH, O. or =O by reaction with a nucleophilic agent, and Z is selected from the group consisting of a $C_{1-20}$ aliphatic group, a monocyclic aromatic group, a bicyclic aromatic group, a multicyclic aromatic group, a $C_{1-20}$ alicyclic group, a noncarbon/nonoxygen moiety, a carbohydrate, a lipid, a nucleic acid and a protein. Preferably, the aromatic group comprises a 5- or 6-membered structure in which each member is independently selected from the group consisting of carbon and a heteroatom. Preferred heteroatoms in the aromatic group include nitrogen, oxygen, sulfur, phosphorus and boron. The noncarbon/nonoxygen moiety preferably comprises a member selected from the group consisting of boron, sulfur, phosphorus and nitrogen. $R_2$, $R_3$, $R_4$ and $R_5$ are independently selected from the group consisting of a $C_{1-20}$ alkyl group, a $C_{2-20}$ alkenyl group, a $C_{2-20}$ alkynyl group, and —$CH_2$—[CR'R"]$_m$—$CH_3$, wherein R' is selected from the group consisting of hydrogen, a $C_{1-20}$ aliphatic group, a monocyclic aromatic group as described above, a bicyclic aromatic group as described above, and a multicyclic aromatic group as described above, and R" is selected from the group consisting of hydrogen, a $C_{1-20}$ aliphatic group, a monocyclic aromatic group as described above, a bicyclic aromatic group as described above, and a multicyclic aromatic group as described above, a $C_{1-20}$ alicyclic group, a noncarbon/nonoxygen moiety as described above, a carbohydrate, a lipid, a nucleic acid, and a protein, and $m \leq 30$. $R_2$ and $R_3$ or $R_4$ and $R_5$ can be connected through one or more members, each of which is independently selected from the group consisting of carbon and a heteroatom. $R_6$, $R_7$, $R_8$ and $R_9$ are independently selected from the group consisting of hydrogen, a hydroxyl group, a $C_{1-20}$ aldehydic group, a $C_{1-20}$ keto group, a primary amino group, a secondary amino group, a tertiary amino group, a sulfido group, a disulfido group, a sulfato group, a sulfito group, a sulfonato group, a sulfinato group, a sulfenato group, a sulfamato group, a metal-containing group, wherein the metal is preferably selected from the group consisting of a transition metal and a lanthanide, a silicone group, a halide, a $C_{1-20}$ ester-containing group, a carboxyl group, a phosphato group, a phosphino group, a phosphinato group, a phosphonato group, a $C_{1-20}$ alkyl group, a $C_{2-20}$ alkenyl group, a $C_{2-20}$ alkynyl group, and —$CH_2$—[CR'R"]$_m$—$CH_3$, wherein R' is selected from the group consisting of hydrogen, a $C_{1-20}$ aliphatic group, a monocyclic aromatic group as described above, a bicyclic aromatic group as described above, and a multicyclic aromatic group as described above, and R" is selected from the group consisting of hydrogen, a $C_{1-20}$ aliphatic group, a monocyclic aromatic group as described above, a bicyclic aromatic group as described above, a multicyclic aromatic group as described above, a $C_{1-20}$ alicyclic group, a noncarbon/nonoxygen moiety as described above, a carbohydrate, a lipid, a nucleic acid and a protein, and $m \leq 30$. Any one of $R_6$, $R_7$, $R_8$ and $R_9$ can be attached covalently or noncovalently to a polymer of synthetic or natural origin. In Formula I, one of $R_6$ and $R_7$ and one of $R_8$ and $R_9$ can be absent such that a double bond joins the two carbon atoms to which the remaining R groups are attached. In Formula I, n=0–20, and in Formula II, n=1–20. X is a heteroatom, and $R_{10}$ and $R_{11}$ are independently selected from the group consisting of a $C_{1-20}$ aliphatic group, a monocyclic aromatic group as described above, a bicyclic aromatic group as described above, a multicyclic aromatic group as described above, each as defined above, a $C_{1-20}$ aliphatic/aromatic group, a heteroatomic group, a $C_{1-20}$ ether-containing group, a $C_{1-20}$ keto group, a $C_{1-20}$ aldehydic group, a carboxamido group, a cyano group, an amino group, a carboxyl group, a selenium-containing group, a sulfato group, a sulfito group, a sulfenato group, a sulfinato group, and a sulfonato group. $R_{10}$ and $R_{11}$ can be connected through an aliphatic group and/or an aromatic group, or $R_{10}$ and/or $R_{11}$ can comprise a member selected from the group consisting of a carbohydrate, a lipid, a nucleic acid and a protein. Also provided by the present invention is a composition comprising a nitroxide or a prodrug thereof for use in the above-described method.

DETAILED DESCRIPTION OF THE INVENTION

Figure 1:
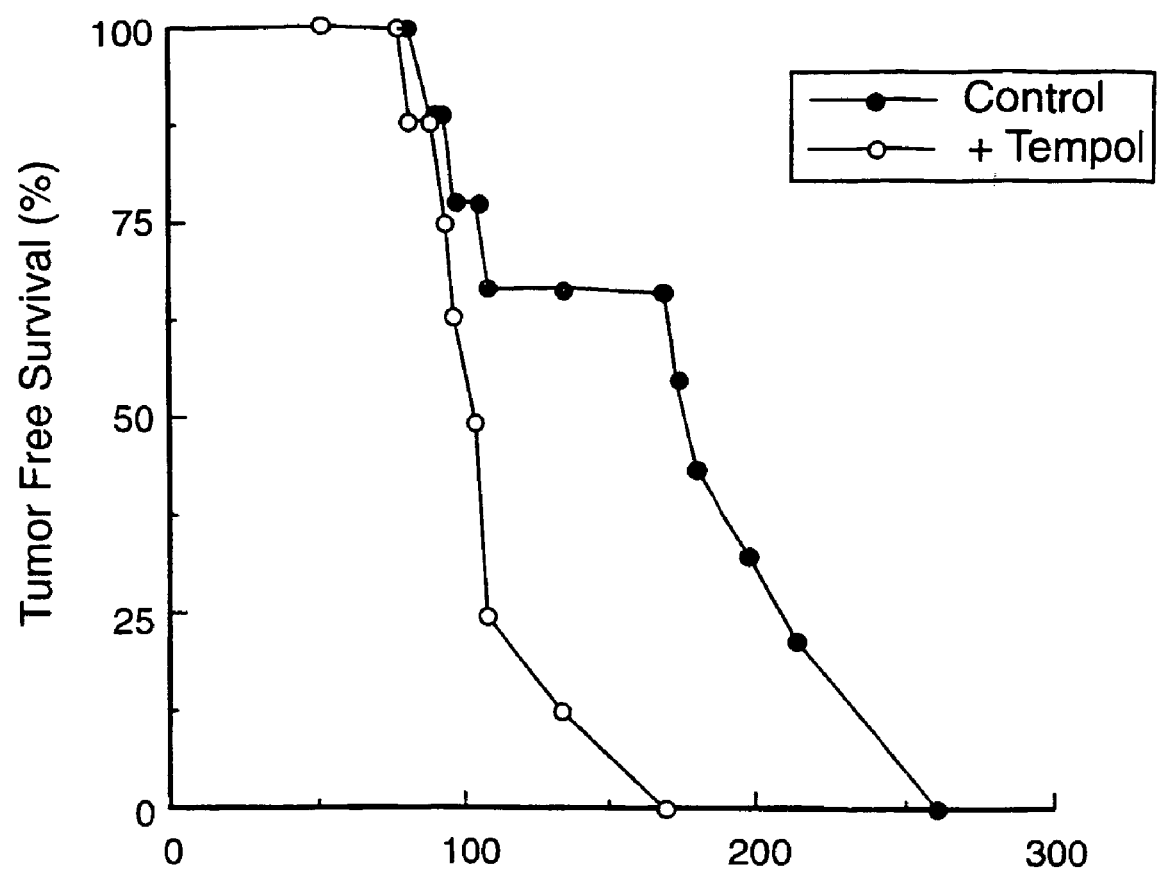
FIG. 1 is a graph of tumor-free survival (%) vs. time (days), wherein open circles represent the control animals and closed circles represent the nitroxide treated animals.

The present invention provides a method for the prophylactic and therapeutic treatment of cancer in an animal, preferably a mammal, more preferably a human. The cancer can be due to a genetic defect, such as a point mutation, an insertion or a deletion, which can be either homozygous or heterozygous, in (i) a tumor suppressor gene, such that the tumor suppressor gene no longer suppresses tumor formation or does so with reduced efficacy, or (ii) a protooncogene, such that the protooncogene is converted to an oncogene, which causes cancer. Examples of inherited genetic defects that predispose humans to developing cancer include, but are not limited to, ataxia telangiectasia, Cowden's disease, Torre's syndrome, Gardner's syndrome, Wiskott-Aldrich syndrome, Peutz-Jeghers syndrome, Bloom's syndrome, Fanconi's syndrome, Werners syndrome, Chediak-Higashi syndrome, retinoblastoma, Beckwith-Wiedeman syndrome, and neuroblastoma. In addition to cancers arising from such inherited genetic defects, genetic defects can be induced by a variety of agents that damage DNA. For example, a number of studies have shown that oxidizing agents (e.g., ionizing radiation and/or oxygen derived free radicals) increase DNA mutations, leading to cancer induction in mammals (see, e.g., Helbock et al., *PNAS USA* 95: 288–293 (1998); Kreutzer et al., *PNAS USA* 95: 3578–3582 (1998); Valentine et al., *Biochemistry* 37: 7030–7038 (1998); McBride et al., *Biochemistry* 30: 207–213 (1991); Reid et al., *Princess Takamatsu Symp.* 22: 221–229 (1991); and Klaunig et al., *Environ. Health Perspect.* 106 (Suppl.): 289–95 (1998)).

Genetic "knock-out" models can be developed for genetic defects in accordance with methods known in the art (Joyner et al., Nature 338: 153–156 (1989); see also Donehower et al. (1992), supra, and Harvey et al. (1993), supra) so as to determine whether or not a cancer caused by such a defect can be prevented, its onset delayed, and/or its progression slowed by a nitroxide or prodrug thereof in accordance with the present invention. Such models then can be used further to determine which nitroxides or prodrugs thereof are particularly effective in the prophylactic and therapeutic treatment of a given cancer, and in what amounts. A genetic "knock-out" model has been developed for ataxia telangiectasia (Barlow et al., *Cell* 86: 159–171 (1996)).

The method of the present invention comprises administering to an animal, preferably a mammal, more preferably a human, at risk for developing a cancer or having a cancer (e.g., a genetic defect or a proclivity for a genetic defect, such as an induced or inherited genetic defect, that promotes or causes cancer), a nitroxide or a prodrug thereof in an amount sufficient to prevent or treat said cancer, respectively, wherein said cancer is susceptible to prevention or treatment with said nitroxide or said prodrug thereof. By "nitroxide" is meant a compound that contains one or more nitroxide groups (i.e., N—O. groups). By "prodrug" is meant a compound that contains at least one functional group that can be converted into a nitroxide group, thereby transforming the prodrug into a nitroxide.

If the cancer is caused by a genetic defect, preferably the genetic defect affects a cancer regulatory gene or a tumor suppressor gene. A cancer regulatory gene is a gene that up-regulates or down-regulates a gene that causes cancer. Examples of such a gene include ABEL and BCL2. A tumor suppressor gene is a gene that suppresses tumor formation, such as the p53 gene, which is preferred.

The nitroxide or prodrug thereof to be administered preferably is alicyclic or heterocyclic. More preferably, the alicyclic or heterocyclic nitroxide or prodrug thereof is a compound of Formula I or Formula II:

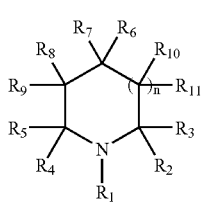

Formula I or

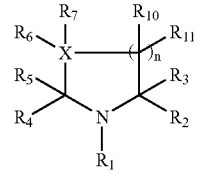

Formula II wherein $R_1$ is selected from the group consisting of H, OH, OZ, O., =O and Y, wherein Y is a leaving group, which can be converted to H, OH, O. or =O by reaction with a nucleophilic agent, and Z is selected from the group consisting of a $C_{1-20}$ aliphatic group, a monocyclic aromatic group, a bicyclic aromatic group, a multicyclic aromatic group, a $C_{1-20}$ alicyclic group, a noncarbon/nonoxygen moiety, a carbohydrate, a lipid, a nucleic acid and a protein. Preferably, the aromatic group comprises a 5- or 6-membered structure in which each member is independently selected from the group consisting of carbon and a heteroatom. Preferred heteroatoms in the aromatic group include nitrogen, oxygen, sulfur, phosphorus and boron. The noncarbon/nonoxygen moiety preferably comprises a member selected from the group consisting of boron, sulfur, phosphorus and nitrogen. $R_2$, $R_3$, $R_4$ and $R_5$ are independently selected from the group consisting of a $C_{1-20}$ alkyl group, a $C_{2-20}$ alkenyl group, a $C_{2-20}$ alkynyl group, and —$CH_2$—$[CR'R'']_m$—$CH_3$, wherein R' is selected from the group consisting of hydrogen, a $C_{1-20}$ aliphatic group, a monocyclic aromatic group as described above, a bicyclic aromatic group as described above, and a multicyclic aromatic group as described above, and R" is selected from the group consisting of hydrogen, a $C_{2-20}$ aliphatic group, a monocyclic aromatic group as described above, a bicyclic aromatic group as described above, a multicyclic aromatic group as described above, a $C_{1-20}$ alicyclic group, a noncarbon/nonoxygen moiety as described above, a carbohydrate, a lipid, a nucleic acid, and a protein, and $m \leq 30$. $R_2$ and $R_3$ or $R_4$ and $R_5$ can be connected through one or more members, each of which is independently selected from the group consisting of carbon and a heteroatom. $R_6$, $R_7$, $R_8$ and $R_9$ are independently selected from the group consisting of hydrogen, a hydroxyl group, a $C_{1-20}$ aldehydic group, a $C_{1-20}$ keto group, a primary amino group, a secondary amino group, a tertiary amino group, a sulfido group, a disulfido group, a sulfato group, a sulfito group, a sulfonato group, a sulfinato group, a sulfenato group, a sulfamato group, a metal-containing group, wherein the metal is preferably selected from the group consisting of a transition metal and a lanthanide, a silicone group, a halide, a $C_{1-20}$ ester-containing group, a carboxyl group, a phosphato group, a phosphino group, a phosphinato group, a phosphonato group, a $C_{1-20}$ alkyl group, a $C_{2-20}$ alkenyl group, a $C_{2-20}$ alkynyl group, and —$CH_2$—$[CR'R'']_m$—$CH_3$, wherein R' is selected from the group consisting of hydrogen, a $C_{1-20}$ aliphatic group, a monocyclic aromatic group as described above, a bicyclic aromatic group as described above, and a multicyclic aromatic group as described above, and R" is selected from the group consisting of hydrogen, a $C_{1-20}$ aliphatic group, a monocyclic aromatic group as described above, a bicyclic aromatic group as described above, a multicyclic aromatic group as described above, a $C_{1-20}$ alicyclic group, a noncarbon/nonoxygen moiety as described above, a carbohydrate, a lipid, a nucleic acid and a protein, and $m \leq 30$. Any one of $R_6$, $R_7$, $R_8$ and $R_9$ can be attached covalently or noncovalently to a polymer of synthetic or natural origin. In Formula I, one of $R_6$ and $R_7$ and one of $R_8$ and $R_9$ can be absent such that a double bond joins the two carbon atoms to which the remaining R groups are attached. In Formula I, n=0–20, and in Formula II, n=1–20. X is a heteroatom, and $R_{10}$ and $R_{11}$ are independently selected from the group consisting of a $C_{1-20}$ aliphatic group, a monocyclic aromatic group as described above, a bicyclic aromatic group as described above, a multicyclic aromatic group as described above, a $C_{1-20}$ aliphatic/aromatic group, a heteroatomic group, a $C_{1-20}$ ether-containing group, a $C_{1-20}$ keto group, a $C_{1-20}$ aldehydic group, a carboxamido group, a cyano group, an amino group, a carboxyl group, a selenium-containing group, a sulfato group, a sulfito group, a sulfenato group, a sulfinato group, and a sulfonato group. $R_{10}$ and $R_{11}$ can be connected through an aliphatic group and/or an aromatic group, or $R_{10}$ and/or $R_{11}$, can comprise a member selected from the group consisting of a carbohydrate, a lipid, a nucleic acid and a protein. The aliphatic group can be branched, substituted and/or unsaturated. If the aliphatic group is substituted, preferably it is substituted with a heteroatom, which is preferably selected from the group consisting of oxygen, phosphorus, selenium, sulfur and nitrogen. The aromatic group can be substituted. If the aromatic group is substituted, preferably it is substituted with a heteroatom, which is preferably selected from the group consisting of nitrogen, oxygen, sulfur, phosphorus and boron. The alicyclic group can be substituted and/or unsaturated. If the alicyclic group is substituted, preferably it is substituted with a heteroatom. The amino group also can be substituted. If the amino group is substituted, preferably it is substituted with up to three substituents selected from the group consisting of a $C_{1-20}$ aliphatic group, a monocyclic aromatic group, a bicyclic aromatic group, a multicyclic aromatic group, and a $C_{1-20}$ alicyclic group, all of which are as described above. Although carbon ranges have been specified for a number of the substituents recited above, such carbon ranges are only preferred, as substituents comprising carbon atoms outside the specified ranges can be effective in the context of the present inventive method.

The above-described method can be adapted for in vitro utilization for scientific and research purposes, including the determination of which types of cancers can be treated by administration of a nitroxide or a prodrug thereof in accordance with the present inventive method. However, the above-described method has particular usefulness in in vivo applications, e.g., in the prevention, delay of onset, and/or slowing of the progression of cancers.

One skilled in the art will appreciate that many suitable methods of administering a nitroxide or a prodrug thereof to an animal, preferably a mammal, more preferably a human, are available, that more than one route can be used to administer a particular compound, and that a particular route can provide a more immediate and more effective treatment than another route. Accordingly, the above-described method is merely exemplary and is in no way limiting.

The dose administered to an animal, preferably a mammal, more preferably a human, with an induced and/or inherited genetic defect that causes or promotes cancer, should be sufficient to prevent cancer, delay its onset, and/or slow its progression. One skilled in the art will recognize that the dosage will depend upon a variety of factors, including the potency of the particular compound employed, and the age, species, condition, and body weight of the animal. The size of the dose will also be determined by the route, timing and frequency of administration, as well as the existence, nature, and extent of any adverse side-effects that might accompany the administration of a particular compound, and the desired physiological effect.

Suitable doses and dosage regimens can be determined by conventional range-finding techniques known to those of ordinary skill in the art. Generally, treatment is initiated with smaller dosages, which are less than the optimal dose of the compound. Thereafter, the dosage is increased by increments until the optimal effect under the circumstances is reached. The present inventive method will typically involve the administration of about 0.1 to about 100 mg of one or more of the compounds described above per kg of body weight.

The present invention also provides a composition comprising a nitroxide or prodrug thereof, preferably an alicyclic or heterocyclic nitroxide or prodrug thereof, more preferably a compound of Formula I or Formula II, as described above. Compounds of Formula I or II can be synthesized according to methods that are well known in the art. See, for example, Rosantzev, "Synthesis of Individual Radicals," Chapter III, pp. 67–89, and "Synthesis of Some Stable Radicals and the Most Important Intermediates," Chapter IX, pp. 203–247, In *Free Nitroxyl Radicals*, Plenum Press (1970). Preferably, the composition is a pharmaceutical composition, which comprises a pharmaceutically acceptable carrier. Any suitably carrier can be used, and will typically be chosen upon consideration of its chemico-physical properties, such as solubility and degree of reactivity with the other components of the composition, and by the route of administration. It will be appreciated by one of skill in the art that, in addition to the following described pharmaceutical composition, the compounds of the present inventive method can be formulated as inclusion complexes, such as cyclodextrin inclusion complexes, or liposomes, for example.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulfonic, for example p-toluenesulfonic acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of excipient will be determined in part by the particular compound, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting. Injectable formulations are among those formulations that are preferred in accordance with the present inventive methods. The requirements for effective pharmaceutical carriers for injectable compositions are well known to those of ordinary skill in the art (See *Pharmaceutics and Pharmacy Practice*, J. B. Lippincott Company, Philadelphia, Pa., Banker and Chalmers, eds., pages 238–250, (1982), and *ASHP Handbook on Injectable Drugs*, Toissel, 4th ed., pages 622–630 (1986)). It is preferred that such injectable compositions be administered intravenously, intratumorally (within the tumor), or peritumorally (near the outside of the tumor). It will be appreciated by one of skill in the art that various of the described injectable compositions are suitable for intratumoral and peritumoral administration.

Topical formulations are well-known to those of skill in the art. Such formulations are suitable in the context of the present invention for application to skin.

Formulations suitable for oral administration can consist of (a) liquid solutions, such as an effective amount of the nitroxide or prodrug thereof dissolved in diluents, such as water, saline, or orange juice; (b) capsules, sachets, tablets, lozenges, and troches, each containing a predetermined amount of the nitroxide or prodrug thereof, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the nitroxide or prodrug thereof, flavoring, for example, sucrose and acacia or tragacanth, as well as pastilles comprising the nitroxide or prodrug thereof in an inert base, such as gelatin and glycerin, or sucrose and acacia, emulsions, gels, and the like containing, in addition to the nitroxide or prodrug thereof, such excipients as are known in the art.

The nitroxides and prodrugs thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The nitroxide or prodrug thereof can be administered in a physiologically acceptable diluent in a pharmaceutical carrier, such as a sterile liquid or mixture of liquids, including water, saline, aqueous dextrose and related sugar solutions, alcohols, such as ethanol, isopropanol, and hexadecyl alcohol, glycols, such as propylene glycol and polyethylene glycol, dimethylsulfoxide, glycerol ketals, such as 2,2-dimethyl-4-hydroxymethyl-1,3-dioxolane, ethers, such as poly(ethylene glycol) 400, oils, fatty acids, fatty acid esters or glycerides, and acetylated fatty acid glycerides with or without the addition of one or more pharmaceutically acceptable surfactants, such as soaps and detergents, suspending agents, such as pectin, carbomers, cellulose derivatives, such as methylcellulose, hydroxypropylmethylcellulose, and carboxymethylcellulose, emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

The parenteral formulations will typically contain from about 0.5 to about 25% by weight of the nitroxide or prodrug thereof in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the nitroxides and prodrugs thereof can be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the nitroxide or prodrug thereof, such carriers as are known in the art to be appropriate.

EXAMPLES

The following examples further illustrate the present invention and, of course, should not be construed as in any way limiting its scope.

Example 1

This example demonstrates that administration of a nitroxide to p53 −/− mice delays the onset of tumors.

Male and female p53 −/− mice (strain 129/Sv-Trp5n $^{tm1\ Tyj}$) were purchased from Jackson Labs (Bar Harbor, Me.). Such animals uniformly die within a few months after birth due to rapid tumor formation and growth. Animals arrived in the laboratory at 7–8 weeks of age, were acclimated for five days and were randomly divided into control (n=8; average weight=24.6 g) and treatment (n=9; average weight=25.0 g) groups. Both groups were allowed food and water ad libitum. The water of the control group was supplemented with sugar (4 g/100 ml), whereas the water of the treatment group was supplemented with sugar (4 g/100 ml) and 4-hydroxy-2,2,6,6-tetramethylpiperidine-1-oxyl (Tempol) to a final concentration of 58 mM. Mice were sacrificed at the first sign of a visible tumor nodule, gross enlargement of the spleen or marked difficulty in breathing. The results are shown in FIG. 1, which is a graph of tumor-free survival versus time (days), in which closed circles represent the control group and open circles represent the treated group. Daily administration of Tempol to p53 −/− mice extended their life span by approximately 48% as compared to the control group. The Tempol-treated animals ultimately developed tumors, but the onset of tumor formation was delayed as compared to the control group.

Example 2

This example demonstrates that administration of a nitroxide to normal C3H female mice for their entire lifespan decreases the incidence of cancer in such mice.

Female C3H mice were supplied through the Frederick Cancer Research Center-Animal Production, Frederick, Md. Animals were received at 6 weeks of age and were randomly divided into groups (n=20/group) as follows: Control-1, which received regular food and water; Control-2, which received regular food and water supplemented with sugar (4 g/100 ml); Tempol/1 Year, which received regular food and water supplemented with sugar (4 g/l 00 ml) and Tempol to a final concentration of 58 mM for one year, after which they were converted to regular food and water; and Tempol/Entire Life Span, which received regular food and water supplemented with sugar (4 g/100 ml) and Tempol to a final concentration of 58 mM for their entire life span. All groups were allowed food and water ad libitum. All groups were followed for their entire life span. Animals were sacrificed at the first sign of a visible tumor nodule, gross enlargement of spleen, or marked difficulty in breathing. The presence of tumor was confirmed histologically.

Figure 2:
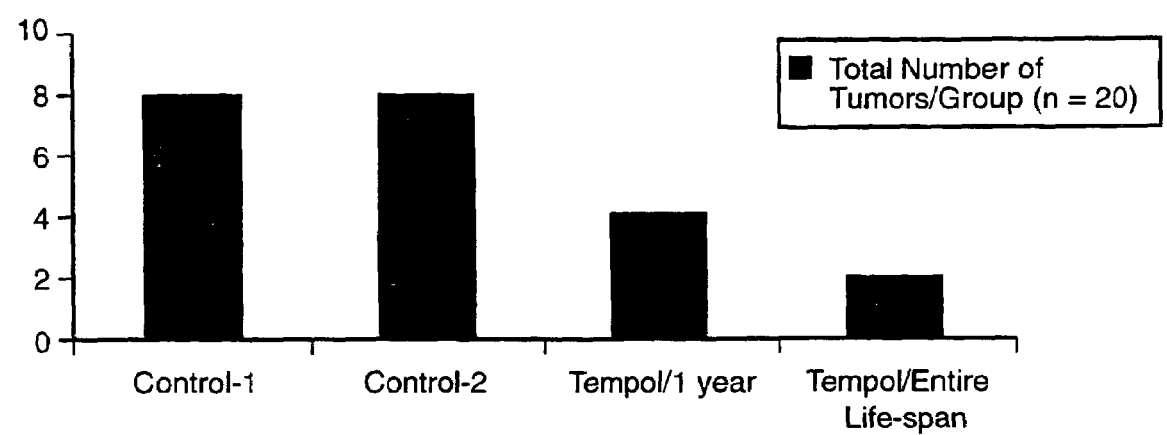
FIG. 2 is a graph of total number of tumors/group (n=20) versus control-1, control-2, Tempol/1 year, and Tempol/entire life span groups.

The results are shown in FIG. 2, which is a graph of the total number of tumors versus the various groups. Administration of Tempol in the drinking water for one year dramatically reduced the incidence of cancer in the treated animals compared to both control groups, and administration of Tempol present in the drinking water for the entire life span of the animals further reduced the incidence of cancer (four-fold reduction compared to controls). Nitroxide treatment effectively reduced the incidence of cancer.

All publications cited herein are hereby incorporated by reference to the same extent as if each publication were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A method of treating Li-Fraumeni syndrome in an animal comprising administering to the animal in need thereof an effective amount of 4-hydroxy-2,2,6,6-tetramethylpiperidine-1-oxyl (tempol) to treat said Li-Fraumeni syndrome.

2. The method of claim 1, wherein said 4-hydroxy-2,2,6,6-tetramethylpiperidine-1-oxyl is administered in an amount of about 0.1 to about 100 mg/kg of body weight of the animal.

3. A method of treating ataxia telangiectasia in an animal comprising administering to the animal in need thereof an effective amount of 4-hydroxy-2,2,6,6-tetramethylpiperidine-1-oxyl (tempol) to treat said ataxia telangiectasia.

4. The method of claim 3, wherein said 4-hydroxy-2,2,6,6-tetramethylpiperidine-1-oxyl is administered in an amount of about 0.1 to about 100 mg/kg of body weight of the animal.

* * * * *